United States Patent [19]

Rohr et al.

[11] Patent Number: 5,057,158

[45] Date of Patent: Oct. 15, 1991

[54] ETHYL CAMPHOLENATES AND DIHYDRO DERIVATIVES THEREOF AS FLAVORANTS AND ODORANTS

[75] Inventors: Martin Rohr, Glen Rock; Cormack Flynn, Ramsey, both of N.J.

[73] Assignee: Givaudan Corporation, Clifton, N.J.

[21] Appl. No.: 913,818

[22] Filed: Sep. 30, 1986

[51] Int. Cl.$^5$ .................. A24D 3/12; A24D 15/30
[52] U.S. Cl. .................................. 131/276; 426/534
[58] Field of Search ............ 131/276; 426/534, 538

[56] References Cited

U.S. PATENT DOCUMENTS 4,547,315  10/1985  Rohr et al. .

OTHER PUBLICATIONS

K. Arata et al., Chemistry Letters (1979) 1017–18.
P. Boyle et al., J. Chem. Soc., (1971) 2136–42.
J. Cason et al., J. Org. Chem. 32 (1967) 575–581.
J. Van Kregten, Recueil 36, (1971) 64–79.
F. Tiemann, Berichte 30 (1897) 242–247.
H. Obermann, Dragoco Report 25, (3) (1978) 54–60.
H. U. Warnecke, Dragoco Report (Ger. Ed.) 1978 25(9) 192–5.
D. DeRijke et al., Perfumer & Flavorist 7, (1982) 31–37.
S. Arctander, "Perfume and Flavor Materials of Natural Origin", Elizabeth, N.J. (1960) 168; 169; 326–328.
F. Tieman, Berichte 29, (1896) 3006–3014.
F. Mahla, Berichte 33, (1900) 1929–1932.

*Primary Examiner*—V. Millin
*Attorney, Agent, or Firm*—Robert F. Tavares; Linda A. Vag

[57] ABSTRACT

The ethyl esters of $\beta$- and $\gamma$-campholenic acids and of $\gamma$-campholenic acid in admixture with $\alpha$-campholenic acid and the ethyl esters of the corresponding dihydro derivatives have organoleptic properties which make them useful for preparing fragrances and flavors.

14 Claims, No Drawings

ETHYL CAMPHOLENATES AND DIHYDRO DERIVATIVES THEREOF AS FLAVORANTS AND ODORANTS

BACKGROUND OF THE INVENTION

The art of creating flavors or fragrances involves blending a number of substances having individual characteristics to produce a composition which has the desired organoleptic effect. A successful product is not simply a combination of pleasant smelling or pleasant tasting materials; a successful product is one in which the individual character of each of the components is not readily perceived per se, but blends with each of the other odor or flavor notes to provide a single organoleptic impression.

To create this single organoleptic impression, the flavorist or perfumer uses a number of compounds which not only contribute their own characteristic odor or flavor to the blend, but which tie together the other materials used in the composition to form a more uniformly blended composition. This ability of a chemical to tie together individual contributions of the other materials is often described by the perfumer or flavorist as the ability to add "roundness" or "naturalness" to the composition. There is always a need for compounds which have this ability.

THE INVENTION

The present invention concerns fragrance and flavor compositions comprising alkyl esters of the formula

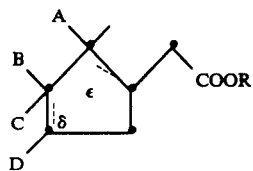

I wherein: R is methyl, ethyl, propyl or butyl, two of the substituents designated by A, B, C and D are methyl groups and the other two are hydrogen, with the proviso that A and D are both methyl or are both hydrogen and B and C are both methyl or are both hydrogen, and, either the dotted line designated by δ or the dotted line designated by ε represents an optional bond, such that, when A and D are methyl the optional bond is represented by δ, and, when B and C are methyl the optional bond is represented by ε.

Propyl and butyl are to be understood as encompassing both the straight chain and branched isomers.

The esters of formula I are derivatives of γ-campholenic acid and β-campholenic acid. These esters are respectively designated by formulas Ia and Ib below, wherein R, δ and ε have the same significance as above.

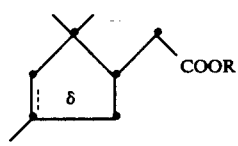

Ia

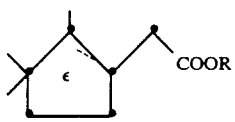

Ib

The methyl and ethyl esters of formula Ia wherein the optional bond represented by δ is present and both possible methyl and ethyl esters of formula Ib are known compounds. [See H. Obermann, Dragoco Report 25 (3), 54 (1978); D. DeRijke et al., Perfumer & Flavorist 7, 31 (1982); F. Tiemann, Berichte 30, 242 (1897); J. R. N. Van Kregten, Recueil 36, 64 (1917); and J. Cason et al., J. Org. Chem. 32, 575 (1967).] The compounds of this invention may be prepared by methods similar to those known in the art.

The compounds of formula I possess organoleptic properties that make them useful as odorants and flavorants.

DESCRIPTION OF THE PREFERRED EMBODIMENTS

The esters of this invention can be prepared by methods known in the art. A preferred method for preparing β-campholenic acid esters Ib, involves the acid catalyzed isomerization of α-campholenic aldehyde to β-campholenic aldehyde followed by oxidation to β-campholenic acid (e.g. chromic acid oxidation). The β-campholenic acid is then esterified using the appropriate alcohol and an acid catalyst. These alkyl β-campholenates can be hydrogenated to the corresponding alkyl β-campholanates in the presence of a metal catalyst (e.g. 10% Pd/C). The preferred method for making the compounds of structure Ib is illustrated in Scheme I.

SCHEME I

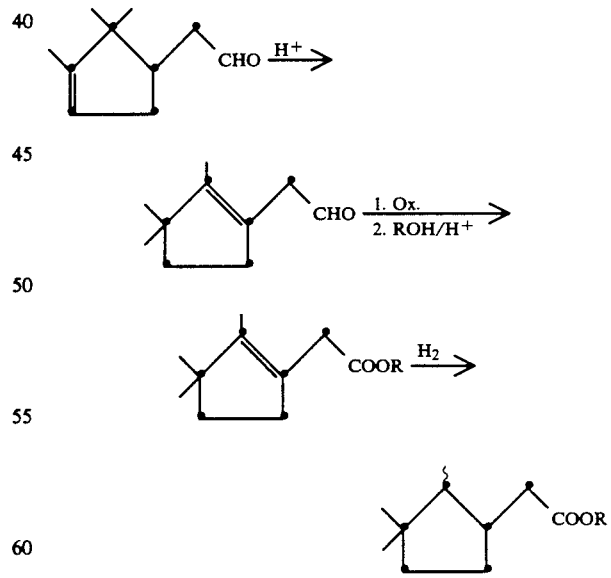

A preferred method for preparing the γ-campholenic acid esters Ia, involves the isomerization of α-pinene oxide over a solid catalyst [e.g. nickel sulfate; see K. Arata et al., Chemistry Letters, 1017 (1979)] and the oxidation of the resulting γ-campholenic aldehyde to γ-campholenic acid (e.g. chromic acid oxidation). The γ-campholenic acid is then esterified using the appropriate alcohol and an acid catalyst. The alkyl γ-campholenates can be hydrogenated to the corresponding alkyl γ-campholanates in the presence of a metal catalyst (e.g. 5% Pd/C). The preferred method for preparing the compounds of structure Ia is illustrated in Scheme II.

SCHEME II

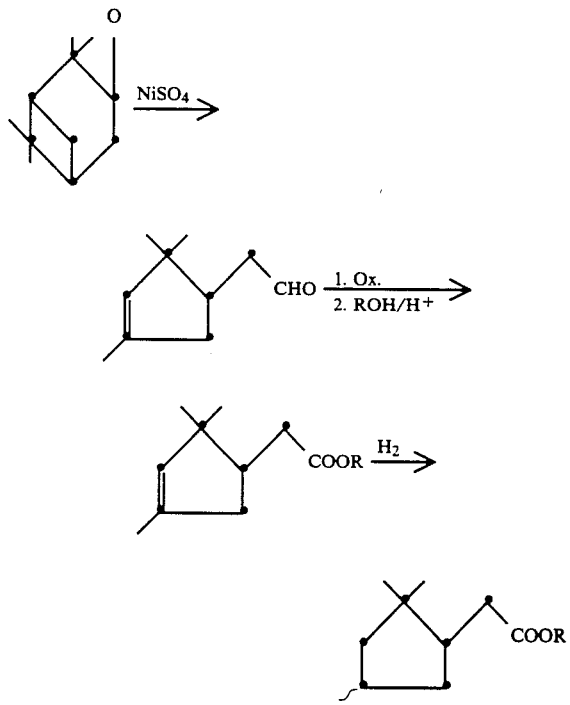

The preferred method for the preparation of γ-campholenic acid esters also yields in admixture with the γ-campholenic acid ester, the α-campholenic acid ester. (See Arata supra.) If desired, the alkyl γ-campholenate may be obtained from this mixture in substantially pure form (i.e. greater than 90% pure) by separation means such as fractional distillation.

The α-campholenic acid esters and the α-campholanic acid esters are represented by formula II below wherein the dotted line designated by μ is an optional bond and R represents a lower alkyl group. U.S. Pat. No. 4,547,315 discloses the use of the alkyl α-campholenates and alkyl α-campholanates as odorants and flavorants.

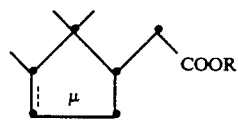

II

The γ-esters of formula Ia are stronger and more odor intense than the α-esters of formula II. The strength of the γ-esters of formula Ia is so much more intense than the α-esters of formula II, that the use of a mixture of the γ- and α-esters for the pure γ-esters provides similar effects, the α-esters serving essentially as diluents.

Table I discloses the organoleptic properties of alkyl γ-campholenates and γ-campholanates of formula Ia.

Table II discloses the organoleptic properties of alkyl β-campholenates and β-campholanates of formula Ib.

TABLE I

| R | Optional Bond | Odor Description | Flavor Description |
|---|---|---|---|
| CH$_3$ | present | fruity, camphoraceous, cherry, animal | fermented, woody vinous |
| C$_2$H$_5$ | present | fruity, berry | sweet, fruity, berry |
| CH$_3$ | absent | fruity, banana, strawberry, blueberry, guava | fruity, woody, banana, berry |
| C$_2$H$_5$ | absent | fruity, resinous, labdanum | sweet, fruity, woody, berry |

Esters Of Formula Ia

TABLE II

| R | Optional Bond | Odor Description | Flavor Description |
|---|---|---|---|
| CH$_3$ | present | fruity, etherial, woody, anise | fruity, woody berry |
| C$_2$H$_5$ | present | fruity, berry, resinous | fruity, woody, winey, berry |
| n-C$_4$H$_9$ | present | weak, woody, oily | weak, fruity, waxy |
| CH$_3$ | absent | fruity, green | fruity, vinous, sweet, berry |
| C$_2$H$_5$ | absent | fruity, berry jammy, strawberry | woody, fruity, winey, berry |

Esters Of Formula Ib

The esters of formula I and the novel mixtures of the esters of formulas Ia and II have organoleptic properties that make them useful in fragrance and flavor compositions, especially flavors of the fruity type and fragrances of the fruity and floral types. Each ester or mixture of esters has its own unique fragrance and flavor properties and each is useful to add "roundness" or "naturalness" to a variety of compositions. The ethyl esters are definitely preferred for use in both flavors and fragrances because of their distinct superiority to the others. They have an outstanding ability to provide "roundness" and "naturalness" to both flavors and fragrances. These ethyl esters have a strong natural berry-like character and are more berry-like, more rounded and generally more preferred than the methyl esters. They are also more intense, more natural and more berry-like than the propyl and butyl analogs.

While the compounds of formula I and the mixtures of the compounds of formula Ia and II can be used to contribute interesting fragrance and/or flavor properties to a composition, they are especially valuable, particularly the ethyl esters, for blending diverse notes in a flavor or fragrance composition. By a blending of diverse notes, we refer to the situation wherein the practitioner has made a basic blend of ingredients, each of which contributes its own character, and finds that a number of different impressions are recognized. In order to achieve the goal of a single and uniform sensory impression, a modifier must be added to bring together their diverse organoleptic impressions into a blended composition which creates a single and uniform impression.

A number of examples have been provided in this application to illustrate the use of the ethyl esters to blend frangrance compositions and add roundness and naturalness. For example, in an iris base, the addition of one of the ethyl esters had the effect of blending the ionone and jasmin aromatic notes. A fragrance composition which was more uniform, more natural, and more reminiscent of the odor produced by the flower was produced. When used in a rose base, the ethyl esters provided fruity nuances which blended with floral notes to provide a more natural and better blended impression which was more reminiscent of the odor produced by the flower itself. In each instance, the fragrance with the ethyl esters was better blended, rounder and more natural. This ability to blend was perhaps best illustrated in a soap fragrance. A typical soap fragrance normally contains high impact chemicals having odors which, because of their intensity, are often described as harsh. Addition of the ethyl esters softened the harsh impression produced by the high impact chemicals and imparted a natural fruity odor which blended with and emphasized the floral notes of the fragrance.

Effects of a similar nature can be illustrated in flavor compositions. For example, a blueberry flavored drink was found to have more body, sweetness and be more reminiscent of a natural blueberry upon the addition of the ethyl esters. Similarly, a grape drink containing the esters was found to be more natural tasting, well-rounded and more grape-like in character. Similar effects can be achieved, when the esters are added to non-berry flavors such as vanilla.

When used in smoking tobacco, the ethyl esters improved the quality of the smoking by improving the sensation in the mouth (mouth feel). The smoking was described as being smoother and as leaving the mouth with an increased and desirable sensation of moistness.

Because of their ability to unite and blend a number of diverse and different notes, the compounds of this invention can be used in a wide variety of fragrance types and their use is limited only by the imagination and skill of the perfumer. It appears, however, that these chemicals are especially suitable for use in floral and fruity type compositions.

Depending on the frangrance composition and the compound used, concentrations as low as 0.0001% can be used for the preferred ethyl esters. A preferred range for the ethyl esters would be from 0.0005% to 50%. The lower range (0.001% to 2%) is preferred when the compounds are principally used to modify and blend diverse odor notes while the upper range, anywhere from 2% to 50%, is preferred when the compound is to serve as a major odor contributor. Higher concentrations, even as high as 95% may be used to produce special effects.

Fragrance compositions containing the compounds of the invention can be used as odorant bases for the preparation of perfumes and toilet waters by adding the usual alcoholic and aqueous diluents thereto. Approximately 15-40% by weight of base would be used for perfumes and approximately 3-5% by weight would be used for toilet waters.

Similarly, the fragrance compositions can be used to odorize soaps, detergents, cosmetics, or the like. In these instances, a base concentration of form about 0.5% to about 2% by weight can be used.

The esters of this invention can be added to foodstuffs, drinks and/or luxury consumables per se, or they can be used to prepare flavoring compositions which are to be added thereto. A flavoring composition is comprised of a mixture of flavor imparting substances and perhaps a diluent, carrier and/or other adjuvants. These flavoring mixtures are then used to impart flavors to foodstuffs. Depending on the ester used, the flavor desired and the foodstuff to be flavored, the amount of the ester of this invention used in the flavor composition can vary over a wide range. The compounds of this invention may be as little as 0.001% of the flavor imparting substances present. In most applications, however, the ester would be at a level of about 0.01% to 1.0% of the flavor imparting substances present. Levels as high as 10% may be desirable in some applications and, as have been mentioned above, the ester itself may be added to foodstuffs to improve, enhance and/or alter the flavor.

The flavoring substances described above are added to or incorporated into the foodstuffs to be flavored using methods well known in the art. The amount of flavoring composition used will depend on the flavor to be imparted and the foodstuff flavored. The amount of the compounds of this invention used in the foodstuffs can be as little as 0.01 parts per million to as much as 100 parts per million. In most foodstuffs, the level of ester used will be in the range of about 0.1 parts per million to about 10 parts per million.

Such foodstuffs are intended to include, but are not limited to chewing gums, candies, jellies, gelatins, desserts, liquors, yogurts, teas, and the like.

The use of the compounds of this invention in tobacco or tobacco products is intended to include, but not be limited to, tobacco itself, tobacco by-products such as reconstituted and homogenized leaf and stem, tobacco surrogates such as lettuce and cabbage leaf, tobacco processing materials such as paper, filters, etc., and flavoring substance compositions used for tobacco products.

In flavoring tobacco or tobacco products, the preferred range would be between 100 ppm and 250 ppm of the tobacco or tobacco substitute used with 175 ppm to 225 ppm being especially preferred.

The claims are to be understood as not encompassing the use of natural materials (e.g., plants or oils extracted therefrom) which may contain an ester of this invention along with many other compounds of said natural materials and which have not been processed for the purpose of increasing the concentration of the esters of this invention to a point where the processed material can be used as a substitute for said esters contained therein.

ILLUSTRATION OF THE PREFERRED EMBODIMENTS

The following examples are provided to illustrate further the practice of the present invention and should not be construed as limiting.

Gas-liquid chromatography (GLC) was used to analyze the products.

EXAMPLE I

Preparation of Alkyl Esters of $\beta$-Campholenic Acid

A. 2,3,3-Trimethyl-1-cyclopentene-1-acetaldehyde ($\beta$-campholenic aldehyde)

A solution of $\alpha$-campholenic aldehyde (550 g) and 85% phosphoric acid (3 g) in toluene (1.5 liters) was stirred at 105° C. for 5 hours under an atmosphere of nitrogen. The cooled mixture was washed with water (2×1 liter) and concentrated to give 490 g of crude oil. Fractionation through an 18" glass packed column gave 150 of a colorless liquid; bp 68°-74° C. @ 6.0 mm Hg; analysis: (CW 20M fused silica column, 100°-190° C.; 5° C./min.) 85% $\beta$-campholenic aldehyde.

B. 2,3,3-Trimethyl-1-cyclopentene-1-acetic acid (β-campholenic acid)

A solution was made of β-campholenic aldehyde (150 g) in acetone (2 liters) and cooled to 0° C. Oxidizing agent was prepared from 169 ml conc. sulfuric acid, 736 ml water and 292 g of sodium dichromate ($Na_2Cr_2O_7 \cdot 2H_2O$). The reagent (375 ml) was added to the solution at 0° C. over a period of 30 minutes. After an additional 15 minutes at 0° C. the acetone was removed by decantation and the residual chromium salts were washed with an additional 200 ml acetone. The combined acetone solution was concentrated, the residue taken up in 10% aqueous sodium hydroxide (1 liter) and the solution washed with $CH_2Cl_2$ (2×1 liter). The aqueous phase was acidified with 25% sulfuric acid followed by extraction with $CH_2Cl_2$ (2×1 liter). Concentration of the dried $CH_2Cl_2$ solution yielded an oil (73 g) which was distilled under reduced pressure to give 53 g of a yellowish liquid; bp 102° C. @ 1.1 mm Hg; crystallized upon standing; analysis: (CW 20M fused silica column, 190° C.) 96% β-campholenic acid.

C. 2,3,3-Trimethyl-1-cyclopentene-1-acetic acid ethyl ester (ethyl β-campholenate)

A solution of β-campholenic acid (10 g) and p-toluenesulfonic acid (1 g) in ethanol (500 ml) was kept at reflux (78° C.) for 5 hours, while the condensate was perculated through a layer of molecular sieves (3 Å) (40 g). The alcohol was then removed, the residue taken up in $CH_2Cl_2$ (500 ml) and the solution extracted with ice cold 5% aqueous sodium hydroxide (500 ml) and water (2×500 ml). Concentration of the dried $CH_2CL_2$ solution gave a crude oil (12 g) which was distilled through a 3" Vigreux column to give 8.5 g of a colorless liquid; bp 58° C. @ 0.8 mm Hg; analysis: (CW 20M fused silica column, 120°-190° C.; 5° C./min.) 96% ethyl β-campholenate; odor: fruity, berry, resinous; flavor: fruity, woody, winey, berry.

The following corresponding β-campholenates were prepared from the appropriate alcohol in a manner similar to that described for the ethyl ester. The structure of each was confirmed by mass spectroscopy, infrared spectroscopy and proton magnetic resonance.

methyl β-campholenate; odor: fruity, etherial, woody, anise; flavor: fruity, woody, berry.

n-butyl β-campholenate; odor: weak, woody, oily; flavor: weak, fruity, waxy.

EXAMPLE II

Preparation of Alkyl Esters of β-Campholanic Acid

A. 2,3,3-Trimethylcyclopentane-1-acetic acid ethyl ester (ethyl-β-campholanate)

Ethyl β-campholenate (3.0 g), prepared as described in Example 1, was hydrogenated in 50 ml of ethanol at 50 psi at 40° C. in the presence of 10% palladium on carbon (0.5 g) using a Parr hydrogenator. When hydrogen uptake ceased, the mixture was filtered and concentrated. The resultant crude product was purified by bulb-to-bulb distillation at 110° C. @ 1 mm Hg to yield 2.5 g of a colorless liquid; analysis: (CW 20M fused silica column, 120°-190° C.; 5° C./min.) 98% ethyl β-campholanate as a mixture of stereoisomers; odor: fruity, berry, jammy, strawberry; flavor: woody, fruity, winey, berry.

The corresponding methyl β-campholanate was prepared from methyl β-campholenate in a manner similar to that described for the ethyl ester. The structure was confirmed by mass spectroscopy, infrared spectroscopy and proton magnetic resonance; odor: fruity, green; flavor: fruity, vinous, sweet, berry.

EXAMPLE III

Preparation of Alkyl Esters of γ-Campholenic Acid

A. 2,2,4-Trimethyl-3-cyclopentene-1-acetaldehyde (γ-campholenic aldehyde)

Nickel sulfate (330 g), which had been activated by calcining its hexahydrate at 220° C. for 16 hours, was suspended in toluene (2.5 liters). α-Pinene oxide (500 g) was fed in at room temperature under vigorous stirring. The mixture was heated and kept at reflux (111° C.) for 90 min. and was then cooled and filtered. The cooled, filtered solution was then concentrated and the crude oil (505 g) fractionated through a 9" glass packed column to give 225 g of a colorless liquid; bp 68°-75° C. @ 2.5 mm Hg; analysis: (CW 20M fused silica column, 100°-190° C.; 5° C./min.) 40% γ-campholenic aldehyde and 35% α-campholenic aldehyde.

B. 2,2,4-Trimethyl-3-cyclopentene-1-acetic acid (γ-campholenic acid)

A solution was made of a mixture (225 g) of 40% γ-campholenic aldehyde and 35% α-campholenic aldehyde in acetone (2 liters) and cooled to 0° C. Oxidizing agent was prepared from 169 ml conc. sulfuric acid, 736 ml water and 292 g of sodium dichromate ($Na_2Cr_2O_7 \cdot 2H_2O$). The reagent (550 ml) was added to the solution at 0° C. over a period of 30 minutes. After an additional 15 minutes at 0° C. the acetone was removed by decantation and the residual chromium salts were washed with an additional 200 ml acetone. The combined acetone solution was concentrated, the residue taken up in 10% aqueous sodium hydroxide (1 liter) and the solution washed with $CH_2Cl_2$ (2×1 liter). The aqueous phase was acidified with 25% sulfuric acid followed by extraction with $CH_2Cl_2$ (2×1 liter). Concentration of the dried $CH_2Cl_2$ solution yielded an oil (142 g) which was distilled under reduced pressure to give 99 g of a yellowish liquid; bp 107° C. @ 1.0 mm Hg; analysis: (CW 20M fused silica column, 190° C.) 56% γ-campholenic acid and 43% γ-campholenic acid.

C. 2,2,4-Trimethyl-3-cyclopentene-1-acetic acid ethyl ester (ethyl γ-campholenate)

A solution containing a mixture (99 g) of γ-campholenic acid (56%) and α-campholenic acid (43%), p-toluenesulfonic acid (2 g), ethanol (750 ml) and heptane (750 ml) was kept at reflux (71° C.) for 16 hours, while the condensate was perculated through a layer of molecular sieves (3 Å) (100 g). The solvent was then removed, the residue taken up in $CH_2Cl_2$ (1 liter) and the solution extracted with ice cold 5% aqueous sodium hydroxide (1 liter) and water (2×500 ml). Concentration of the dried $CH_2Cl_2$ solution gave a crude oil (115 g), which was distilled through a 9" glass packed column to give 95 g of a colorless liquid; bp 73°-75° C. @ 1.5 mm Hg analysis: (CW 20M fused silica column, 120°-190° C.; 5° C./min.) 60% ethyl γ-campholenate and 40% ethyl α-campholenate; odor: fruity, berry; flavor: sweet, fruity, berry.

Careful fractionation of a mixture composed of 60% ethyl γ-campholenate and 40% ethyl α-campholenate through a 9" glass packed column gave a product, bp 70° C. 1 mm/Hg, consisting of 91% ethyl γ-campholenate and 9% of the ethyl α-campholenate; odor: fruity, berry; flavor: sweet, fruity, berry.

Ethyl γ-campholenate of 99% purity was obtained by a preparative gas-liquid chromatography separation of a mixture of the γ- and α-isomers (CW 20M 6'×¼" column, 120° C.).

The following corresponding campholenates were prepared from the appropriate alcohol in a manner similar to that described for the ethyl ester. The structure of each was confirmed by mass spectroscopy, infrared spectroscopy and proton magnetic resonance.

methyl γ-campholenate; odor: fruity, camphoraceous, cherry, animal; flavor: fermented, woody, vinous.

3:2 mixture of n-butyl γ-campholenate and n-butyl α-campholenate; odor: pencil, cedar; flavor: weak, vinous, woody.

EXAMPLE IV

Preparation of Alkyl Esters of γ-Campholanic Acid

A. 2,2,4-Trimethylcyclopentane-1-acetic acid ethyl ester (ethyl γ-campholanate)

Ethyl γ-campholenate (2 g; purity 91%), prepared as described in Example III, was hydrogenated in 50 ml of ethanol at 50 psi and room temperature in the presence of 5% palladium on carbon (0.5 g) using a Parr hydrogenator. When hydrogen uptake ceased, the mixture was filtered and concentrated. The resultant crude product was purified by bulb-to-bulb distillation at 120° C. @ 2.7 mm to give 1.8 g of a colorless liquid; analysis: (CW 20M fused silica column, 120°-190° C.; 5°/min.) 91% ethyl γ-campholanate (mixture of stereoisomers by GLC) and 8% ethyl α-campholanate; odor: fruity, resinous, labdanum; flavor: sweet, woody, fruity, berry.

Ethyl γ-campholanate of 99% purity was obtained by a preparative gas-liquid chromatography separation of a mixture of the γ- and α-isomers (CW 20M 6'×¼" column, 120° C.).

The following corresponding campholanates were prepared from the corresponding alkyl γ-campholenates in a manner similar to that described for the ethyl ester. The structure of each was confirmed by mass spectroscopy, infrared spectroscopy and proton magnetic resonance.

methyl γ-campholanate; odor: fruity, banana, strawberry, blueberry, guava; flavor: fruity, woody, banana, berry.

3:2 mixture of n-butyl γ-campholanate and n-butyl α-campholanate; odor: basil, estragole; flavor: weak, woody, fruity.

EXAMPLE V

Use of Ethyl Campholenates and Campholanates as Odorants

A. Iris Base

| Components | Parts by Weight |
| --- | --- |
| Isoraldeine ®-70 (methylionone mixture) | 100 |
| α-Ionone | 200 |
| Irone Alpha, refined (6-methylionone) | 10 |
| Cinnamon Leaf Oil | 15 |
| Heliotropin | 40 |
| Ylang Oil (Bourbon) | 20 |
| Jasmin Oil (Synthetic) | 25 |
| Methyl Octine Carbonate | 2 |
| Iris Aldehyde (2-nonen-1-al), 10% in dipropylene glycol | 2 |
| Phenyl Ethyl Alcohol | 50 |
| Coumarin | 15 |
| Citronellol | 50 |
| Benzyl Acetate | 10 |
| Total | 539 |

The Iris base formulated as above is found lacking in unity; the odors of isoraldeine ®, α-ionone and irone alpha are not fully integrated with the odors of the rose and jasmin aromatics. The resulting fragrance is dominated by the odor of ionones which give the base a synthetic quality. The addition of 0.2 parts (0.037%) of a mixture of 60% ethyl γ-campholenate and 40% ethyl α-campholenate was found to effectively unite the composition into a more natural, full-bodied, fruity-floral composition. The same desirable effect was achieved with the addition to the base of 200 parts (27%) ethyl α-campholenate in place of the 60/40 mixture of the γ- and α-ethyl esters. When a similar amount (200 parts) of the latter mixture was used in the base the effect achieved was still that of a well-blended composition but the intensity or strength of the sweet-fruity character was markedly increased.

B. Rose Base

| Components | Parts by Weight |
| --- | --- |
| Phenyl Ethyl Alcohol | 350 |
| Citronellol | 200 |
| Geraniol | 300 |
| Viridine ® (phenylacetaldehyde dimethyl acetal) | 5 |
| Guaiacwood concrete | 20 |
| Total | 875 |

The Rose base as formulated above is found thin and lacking in the fruity odors inherent in a natural rose fragrance. The addition of 10 parts (1.1%) of ethyl β-campholanate accented the fruity character of the base, blending into the floral notes and achieving a more natural floral aspect. The same amount (10 parts) of ethyl α-campholenate had the similar desirable effect of adding a fruity character while blending the base. The addition of 10 parts of ethyl γ-campholenate added a fuller fruity-floral character while adding body and lift. When 0.01 parts (0.0011%) of the latter was used the intensity of the odor effect was found to be more similar to that achieved when 10 parts of ethyl α-campholenate was used.

C. Soap Fragrance

| Components | Parts by Weight |
| --- | --- |
| Terpinyl Acetate | 40 |
| Bergamyl Acetate ® (pseudo-linalyl acetate) | 15 |
| Lemonile ® (3,7-dimethyl-2,6-nonadienenitrile) | 1 |
| Linalool (Synthetic) | 20 |
| Ylang Oil (Synthetic) | 15 |
| Benzyl Acetate | 20 |
| Geraniol | 25 |
| Phenyl Ethyl Alcohol | 25 |
| Methyl Phenyl Carbinyl Acetate | 6 |
| Eugenol | 20 |
| Benzyl Salicylate | 150 |
| Sandalore ® [5-(2,2,3-trimethyl-cyclopent-3-en-1-yl)3-methylpentan-2-ol] | 8 |
| Aldehyde C-11, Undecylenic | 3 |
| gamma-Undecalactone | 3 |

-continued

| Components | Parts by Weight |
|---|---|
| Lilial ® (p-t-butyl-α-methylhydrocinnamaldehyde) | 50 |
| Cinnamon Leaf Oil | 2 |
| Ethyl Vanillin | 2 |
| β-Naphthol Ethyl Ether | 10 |
| Thibetolide ® (pentadecanolide) | 45 |
| Cedartone ™ V (acetylcedrene) | 30 |
| p-t-Butylcyclohexyl Acetate | 30 |
| Phenyl Acetic Acid, 10% in dipropylene glycol | 2 |
| Costus Oil (synthetic) | 2 |
| Cumin Oil, 10% in dipropylene glycol | 5 |
| gamma-Nonalactone | 2 |
| Total | 531 |

The soap fragrance formulated above, which is in the direction of carnation-woody-musky, is found to be harsh and somewhat uneven. The floral character of the fragrance is somewhat subdued. The addition of 20 parts (3.6%) of ethyl β-campholenate to the base added a natural fruity effect that rounded out the fragrance, particularly the floralcy of the fragrance. This effect was similarly achieved by the addition of the same amount (20 parts) of ethyl α-campholenate, particularly the effect of accenting the floralcy. When 20 parts of a 60/40 mixture of ethyl γ-campholenate and ethyl α-campholenate was used in the base the intensity of the floral-sweetness was markedly increased. The use of 0.2 parts (0.038%) of the latter mixture was found to be more comparable in effect on the intensity of odor character to that of 20 parts of ethyl α-campholenate. Effects similar to those achieved with a 60/40 mixture of ethyl γ-campholenate and ethyl α-campholenate can be achieved with a similar mixture of ethyl γ-campholenate and ethyl α-campholanate.

EXAMPLE VI

Use of Ethyl Campholenates and Campholanates as Flavorants

A. Artificial Vanilla Flavor

| Components | Parts by Weight |
|---|---|
| Vanillin | 5.0 |
| Heliotropin | 0.2 |
| Veratraldehyde | 0.3 |
| Benzodihydropyrone | 0.2 |
| Ethyl Vanillin | 0.3 |
| Ethanol (95%) | 50.0 |
| Water (distilled) | 44.0 |
| Total | 100.0 |

A taste solution was prepared by adding 0.1 g of the above artificial vanilla flavor to a solution of 100 g of sucrose in 900 g of distilled water. To 100 g of the artificial vanilla flavored taste solution was added 0.1 g of a 0.01% solution of ethyl α-campholenate in ethanol (0.1 ppm in the finished drink). A bench panel of four tasters compared the solution containing the additive to the untreated solution. All preferred the artificial vanilla containing the additive stating that it was creamier, richer in vanilla character, more natural and closer to pure vanilla extract.

Similar results can be achieved with the use of ethyl β-campholenate, ethyl β-campholanate, ethyl γ-campholenate and ethyl γ-campholanate.

B. Artificial Blueberry Flavor

| Components | Parts by Weight |
|---|---|
| Ethyl Acetate | 50.0 |
| cis-3-Hexenol | 10.0 |
| Amyl Butyrate | 5.0 |
| Ethyl Isovalerate | 20.0 |
| Linalool | 10.0 |
| Vanillin | 5.0 |
| Total | 100.0 |

A blueberry flavor solution was prepared by adding 1.0 g of the above blueberry flavor concentrate to 99.0 g of 95% ethanol. A blueberry flavored drink was prepared by adding 2.0 g of the above blueberry flavor solution to 100 g sucrose and 0.5 g malic acid in 899.3 g distilled water. To 500 g of the blueberry flavored drink was added 0.1 g of a 1.0% solution of ethyl α-campholenate in ethanol (approximately 2 ppm in the finished drink). A bench panel of four tasters compared the solution containing the additive to the untreated solution. All preferred the blueberry flavored drink containing the additive stating that it had more body, sweetness and a more natural blueberry flavor.

A blueberry flavored drink containing ethyl γ-campholenate (approximately 2 ppm) was compared to a blueberry flavored drink containing ethyl α-campholenate (approximately 2 ppm) by a bench panel of four tasters. All stated that the drink containing ethyl γ-campholenate was much stronger in aroma and flavor, closer to fresh blueberry in flavor, and much preferred over the drink containing ethyl α-campholenate.

In the same way, test drinks containing ethyl β-campholenate and ethyl β-campholanate were compared to a test drink containing ethyl α-campholenate. The panel stated unanimously that the drinks containing ethyl β-campholenate and ethyl β-campholanate were slightly stronger in aroma and flavor than the drink containing ethyl α-campholenate, and were slightly preferred for blueberry character.

C. Artificial Grape Flavor

| Components | Parts by Weight |
|---|---|
| Methyl Anthranilate | 55.0 |
| Ethyl Anthranilate | 15.0 |
| Ethyl Butyrate | 2.0 |
| Triethyl Citrate | 20.0 |
| Ethyl Acetate | 0.4 |
| Geranyl Acetate | 0.2 |
| Amyl Acetate | 0.1 |
| Geranyl Propionate | 0.2 |
| Ethyl Heptanoate | 2.0 |
| Ethyl Oenanthate | 3.5 |
| Ethyl Pelargonate | 0.5 |
| Ethyl Caproate | 0.2 |
| α-Ionone | 0.2 |
| Amyl Butyrate | 0.2 |
| Ethyl Vanillin | 0.3 |
| Ethyl Propionate | 0.2 |
| Total | 100.0 |

A grape flavor solution was prepared by adding 1.0 g of the above grape flavor concentrate to 99.0 g of 95% ethanol. A grape flavored drink was prepared by adding 2.0 g of the above grape flavor solution to 120 g sucrose and 1.0 g tartaric acid in 877 g distilled water. To 500 g of the grape flavored drink was added 0.05 g of a 1.0% solution of ethyl α-campholenate in ethanol (approximately 1 ppm in the finished drink). A bench panel of four tasters compared the solution containing the additive to the untreated solution. All tasters preferred the grape flavored drink containing the additive stating that it was more natural tasting, well-rounded and more grape-like in character.

A grape flavored drink containing ethyl γ-campholenate (approximately 1 ppm) was compared to a grape flavored drink containing ethyl α-campholenate (approximately 1 ppm) by a bench panel of four tasters. All stated that the drink containing the ethyl γ-campholenate was stronger in aroma and flavor and more preferred over the drink containing ethyl α-campholenate.

In the same way, test drinks containing ethyl β-campholenate and ethyl β-campholanate were compared to a test drink containing ethyl α-campholenate. The panel all stated that the drinks containing ethyl β-campholenate and ethyl β-campholanate were slightly stronger in aroma and flavor, and were slightly preferred in a grape flavored drink.

D. Gelatin Mix

| Components | Parts by Weight |
| --- | --- |
| Gelatin 250 bloom | 6.50 |
| Sucrose | 75.00 |
| Adipic Acid | 2.50 |
| Sodium Citrate | 0.85 |
| Salt | 0.15 |
| Total | 85.00 |

The above components were combined and dissolved in 415 g of hot water. To this gelatin mix was added 1.0 g of the grape flavored solution as prepared in section C above. To 100 g of the grape flavored gelatin mix was added 0.02 g of a 1.0% solution of ethyl α-campholenate in ethanol (approximately 2 ppm in gelatin mix). A bench panel of four tasters compared the grape flavored gelatin mix with and without the additive and found the gelatin mix with the additive was more natural, well-rounded and contained a preferred grape flavoring.

Results similar to those described in section C above can be expected for grape flavored gelatin mixes containing ethyl γ-campholenate, ethyl γ-campholanate, ethyl β-campholenate or ethyl β-campholanate when compared to a grape flavored gelatin mix containing ethyl α-campholenate.

E. Tobacco Product

A standard cigarette blend was prepared as described below:

| Components | Parts by Weight |
| --- | --- |
| Bright Tobacco | 55 |
| Burley Tobacco | 25 |
| Expanded Stems | 5 |
| Reconstituted Leaf | 15 |
| Total | 100 |

Ethyl α-campholenate at 200 ppm was added to cigarettes prepared from the above tobacco blend. The cigarettes with and without the additive were evaluated by smoking. The cigarettes with the additive were found to have enhancement of mouth feel (fullness), smoother mainstream and increased moistness of the mouth.

Similar effects were achieved by the addition of ethyl γ-campholenate, ethyl β-campholenate and ethyl β-campholanate.

Similar effects can also be achieved by the addition of ethyl γ-campholanate.

We claim:

1. A tobacco product comprising a flavoring effective amount of a compound of the formula

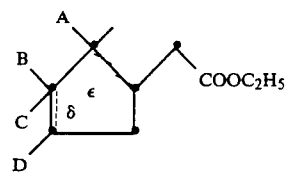

wherein:
two of the substituents designated by A, B, C and D are methyl groups and the other two are hydrogen with the proviso that A and D are both methyl or are both hydrogen and B and C are both methyl or are both hydrogen, and,
either the dotted line designated by δ or the dotted line designated by ε represents an optional bond, such that, when A and D are methyl, the optional bond is represented by δ, and, when B and C are methyl the optional bond is represented by ε.

2. A tobacco product according to claim 1 wherein the compound is 2,2,4-trimethyl-3-cyclopentene-1-acetic acid ethyl ester.

3. A tobacco product according to claim 1 wherein the compound is 2,2,4-trimethylcyclopentane-1-acetic acid ethyl ester.

4. A tobacco product according to claim 1 wherein the compound is 2,3,3-trimethyl-1-cyclopentene-1-acetic acid ethyl ester.

5. A tobacco product according to claim 1 wherein the compound is 2,3,3-trimethylcyclopentane-1-acetic acid ethyl ester.

6. A tobacco product comprising a flavoring effective amount of a mixture consisting essentially of compounds of the formulas

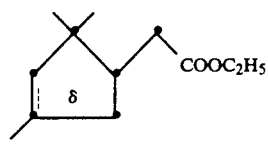

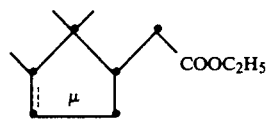

wherein:
δ and μ designate optional bonds represented by the dotted lines with the proviso that the two optional bonds represented by the dotted lines are both present or are both not present, and,
said mixture comprises at least 40% of said compound of formula Ia.

7. A tobacco product according to claim 6 wherein the compound of formula Ia is 2,2,4-trimethyl-3-cyclopentene-1-acetic acid ethyl ester and the compound of formula II is 2,2,3-trimethyl-3-cyclopentene-1-acetic acid ethyl ester.

8. A method for improving the flavor of a flavor composition which comprises adding thereto a flavoring effective amount of a compound of the formula

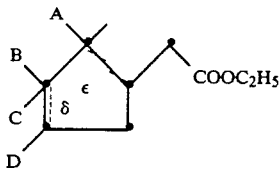

I wherein:
two of the substituents designated by A, B, C and D are methyl groups and the other two are hydrogen with the proviso that A and D are both methyl or are both hydrogen and B and C are both methyl or are both hydrogen, and, either the dotted line designated by δ or the dotted line designated by ε represents an optional bond, such that, when A and D are methyl, the optional bond is represented by δ, and, when B and C are methyl the optional bond is represented by ε.

9. A method according to claim 8 wherein the compound is 2,2,4-trimethyl-3-cyclopentene-1-acetic acid ethyl ester.

10. A method according to claim 8 wherein the compound is 2,2,4-trimethylcyclopentane-1-acetic acid ethyl ester.

11. A method according to claim 8 wherein the compound is 2,3,3-trimethyl-1-cyclopentene-1-acetic acid ethyl ester.

12. A method according to claim 8 wherein the compound is 2,3,3-trimethylcyclopentane-1-acetic acid ethyl ester.

13. A method for improving the flavor of a flavor composition which comprises adding thereto a flavoring effective amount of a mixture consisting essentially of compounds of the formulas

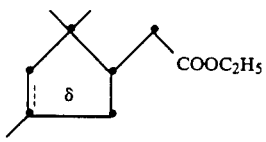

Ia

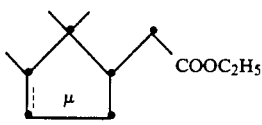

II wherein:
δ and μ designate optional bonds represented by the dotted lines with the proviso that the two optional bonds represented by the dotted lines are both present or are both not present, and,
said mixture comprises at least 40% of said compound of formula Ia.

14. A method according to claim 13 wherein the compound of formula Ia is 2,2,4-trimethyl-3-cyclopentene-1-acetic acid ethyl ester and the compound of formula II is 2,2,3-trimethyl-3-cyclopentene-1-acetic acid ethyl ester.

* * * * *